United States Patent [19]

Blake

[11] Patent Number: 5,643,275

[45] Date of Patent: Jul. 1, 1997

[54] INTRAOCULAR LENS INJECTOR

[75] Inventor: Larry W. Blake, Coto de Caza, Calif.

[73] Assignee: Pharmacia Iovision, Inc., Irvine, Calif.

[21] Appl. No.: 466,037

[22] Filed: Jun. 6, 1995

Related U.S. Application Data

[62] Division of Ser. No. 86,930, Jul. 2, 1993, Pat. No. 5,468,246.

[51] Int. Cl.$^6$ .................................. A61B 17/00; A61F 2/16
[52] U.S. Cl. .................................................. 606/107; 623/6
[58] Field of Search ................................ 623/6; 606/107

[56] References Cited

U.S. PATENT DOCUMENTS

| | | |
|---|---|---|
| 2,761,446 | 9/1956 | Reed . |
| 3,150,406 | 9/1964 | Obitts . |
| 3,703,174 | 11/1972 | Smith . |
| 3,757,781 | 9/1973 | Smart . |
| 3,866,249 | 2/1975 | Flom . |
| 3,991,426 | 11/1976 | Flom et al. . |
| 4,002,169 | 1/1977 | Cupler, II . |
| 4,053,953 | 10/1977 | Flom et al. . |
| 4,122,556 | 10/1978 | Poler . |
| 4,170,043 | 10/1979 | Knight et al. . |
| 4,170,661 | 10/1979 | Knight et al. . |
| 4,190,049 | 2/1980 | Hager et al. . |
| 4,198,980 | 4/1980 | Clark . |
| 4,214,585 | 7/1980 | Bailey, Jr. . |
| 4,253,199 | 3/1981 | Banko . |
| 4,325,375 | 4/1982 | Nevyas . |
| 4,373,218 | 2/1983 | Schachar . |
| 4,573,998 | 3/1986 | Mazzocco . |
| 4,619,657 | 10/1986 | Keates et al. . |
| 4,619,662 | 10/1986 | Juergers, Jr. . |
| 4,681,102 | 7/1987 | Bartell . |
| 4,687,485 | 8/1987 | Lim et al. . |
| 4,699,140 | 10/1987 | Holmes et al. . |
| 4,702,244 | 10/1987 | Mazzocco ........................ 606/107 |
| 4,743,254 | 5/1988 | Davenport . |
| 4,747,404 | 5/1988 | Jampel et al. . |
| 4,759,359 | 7/1988 | Willis et al. . |
| 4,759,763 | 7/1988 | Bissonette et al. . |
| 4,763,650 | 8/1988 | Hauser . |
| 4,765,329 | 8/1988 | Cumming et al. . |
| 4,769,034 | 9/1988 | Poley . |
| 4,781,719 | 11/1988 | Kelman ........................... 623/6 |
| 4,785,810 | 11/1988 | Baccala et al. . |
| 4,791,924 | 12/1988 | Kelman . |
| 4,813,957 | 3/1989 | McDonald . |
| 4,834,094 | 5/1989 | Patton et al. . |
| 4,834,750 | 5/1989 | Gupta ............................. 623/6 |

(List continued on next page.)

FOREIGN PATENT DOCUMENTS

| | | |
|---|---|---|
| 0363213 | 4/1990 | European Pat. Off. . |
| 2604896 | 7/1987 | France . |
| 3610925 | 3/1986 | Germany . |
| 2191439 | 12/1987 | United Kingdom . |
| WO8201646 | 5/1982 | WIPO . |
| WO8910729 | 11/1989 | WIPO . |
| WO9208423 | 5/1992 | WIPO . |

OTHER PUBLICATIONS

Staar Softrans Lens Injector System Brochure, 1991, pp. 1–4.

*Primary Examiner*—Mary Beth Jones
*Attorney, Agent, or Firm*—Knobbe, Martens, Olson & Bear, LLP

[57] ABSTRACT

An intraocular lens injector compresses an intraocular lens by rolling the lens into a tight spiral and injects the compressed lens though a relatively small incision in the eye, approximately 2–3 millimeters in length, resulting from a phacoemulsification procedure. The intraocular lens is inserted into a receiving channel of the injector in an uncompressed state and is urged into a cylindrical passageway. As the intraocular lens advances into the cylindrical passageway, the lens will roll upon itself into a tightly rolled spiral within the confines of the cylindrical passageway. An insertion rod is inserted into an open end of the cylindrical passageway and advances the compressed lens down the passageway. As the lens exits the passageway and enters the eye, the lens will expand back to its uncompressed state.

3 Claims, 13 Drawing Sheets

U.S. PATENT DOCUMENTS

| | | |
|---|---|---|
| 4,836,201 | 6/1989 | Patton et al. . |
| 4,836,202 | 6/1989 | Krasner . |
| 4,844,065 | 7/1989 | Faulkner . |
| 4,862,885 | 9/1989 | Cumming . |
| 4,880,000 | 11/1989 | Holmes et al. . |
| 4,919,130 | 4/1990 | Stoy et al. . |
| 4,934,363 | 6/1990 | Smith et al. . |
| 4,976,716 | 12/1990 | Cumming . |
| 5,066,297 | 11/1991 | Cumming . |
| 5,098,439 | 3/1992 | Hill et al. . |
| 5,100,410 | 3/1992 | Dulebohn . |
| 5,123,905 | 6/1992 | Kelman ................... 606/107 |
| 5,190,552 | 3/1993 | Kelman . |
| 5,190,553 | 3/1993 | Kanert et al. . |
| 5,275,604 | 1/1994 | Rheinish et al. . |
| 5,281,227 | 1/1994 | Sussman . |
| 5,304,182 | 4/1994 | Rheinish et al. . |
| 5,354,333 | 10/1994 | Kammann et al. . |
| 5,376,115 | 12/1994 | Jansen . |

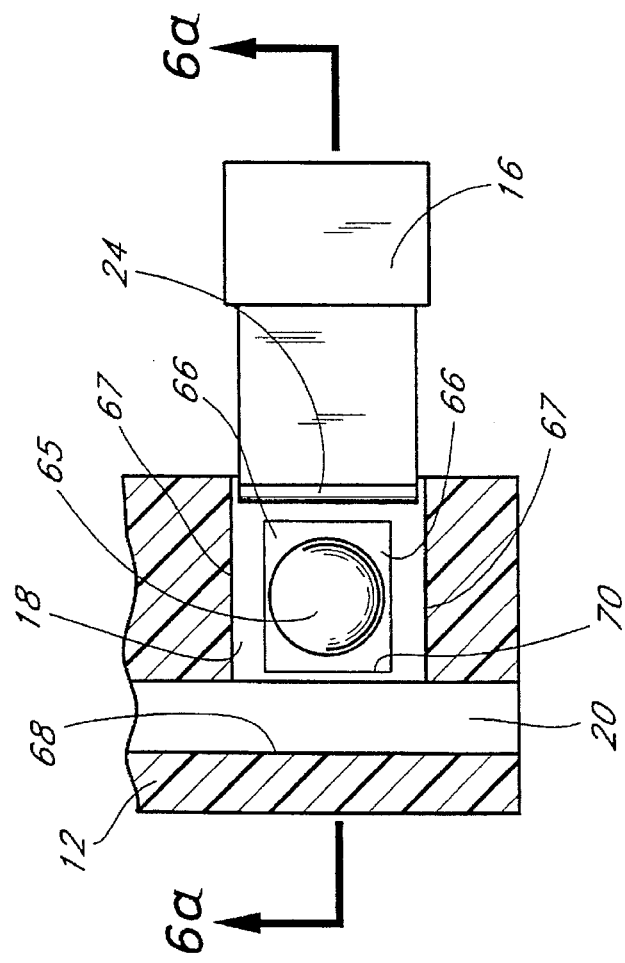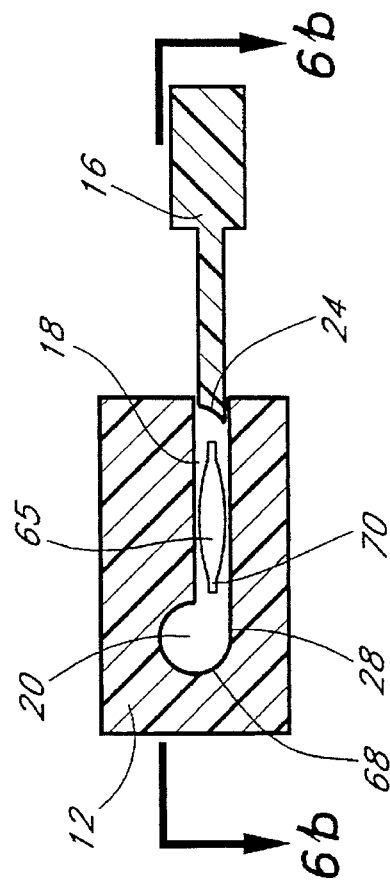

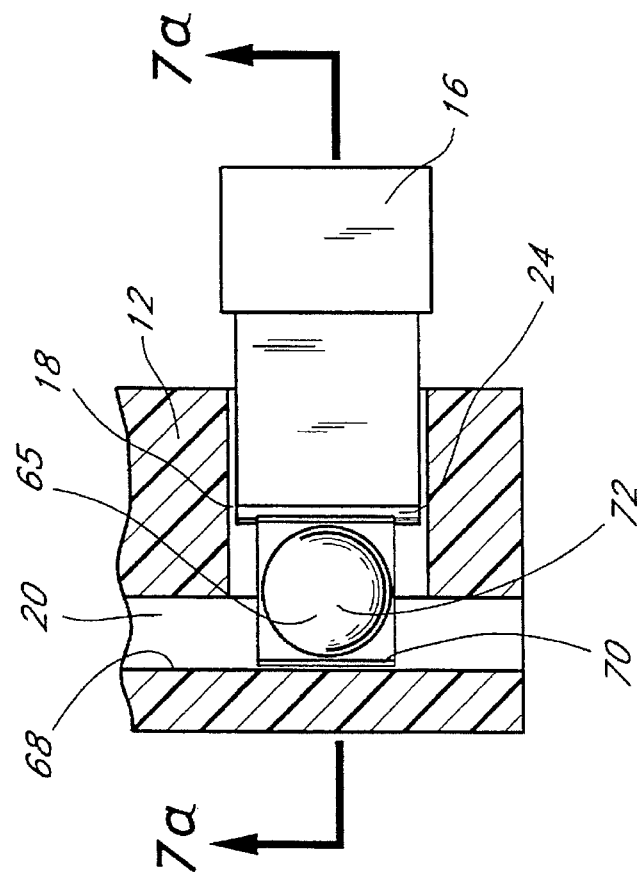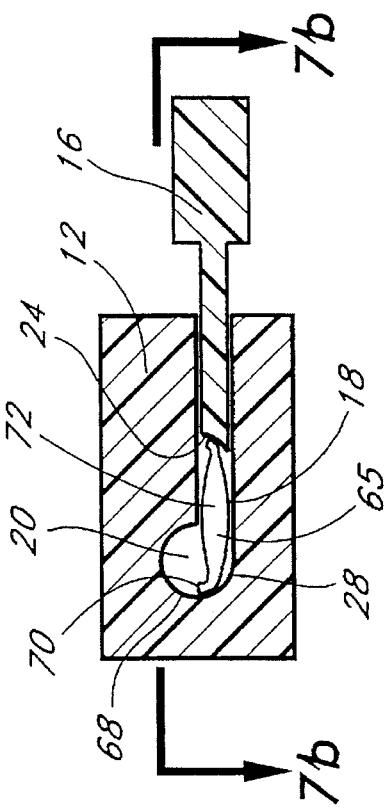

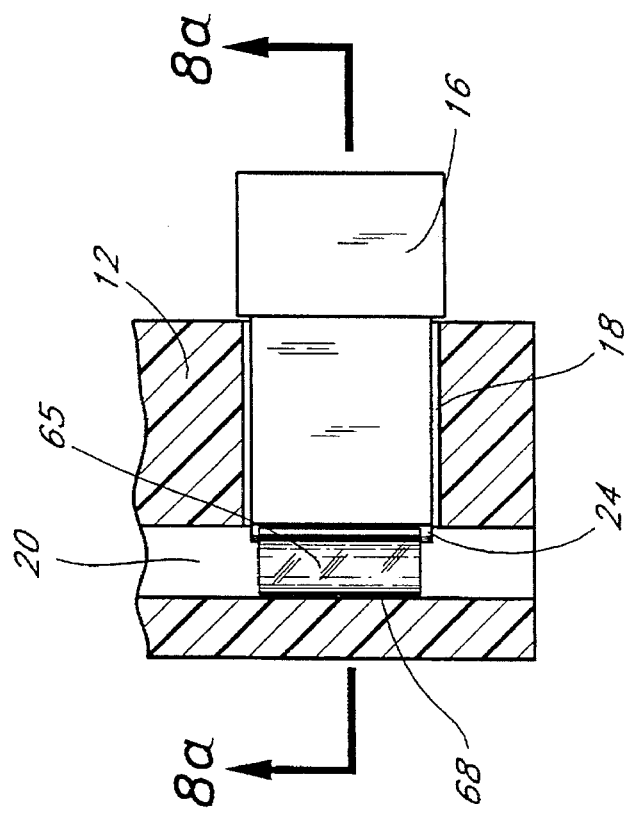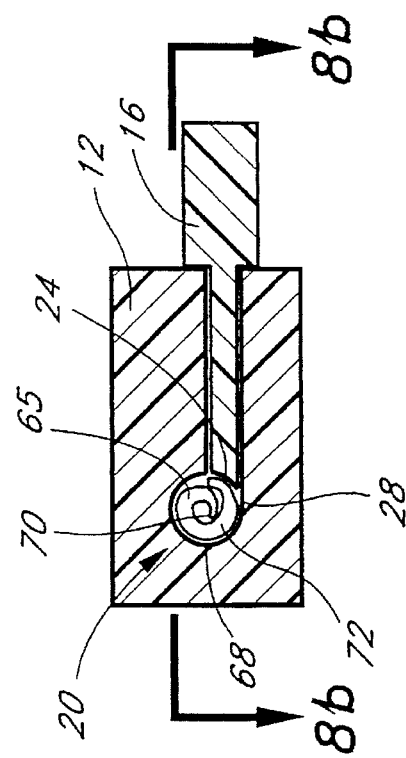

INTRAOCULAR LENS INJECTOR

This application is a divisional application of Ser. No. 08/086,939, filed on Jul. 2, 1993 now U.S. Pat. No. 5,468,246.

BACKGROUND OF THE INVENTION

1. Field of the Invention

The present invention relates to the field of intraocular lens replacement and, more particularly, to the insertion of an artificial intraocular lens into the eye.

2. Description of the Related Art

Artificial intraocular lenses, used to replace damaged or diseased natural lenses in the eye, have been widely accepted in the last several decades. Typically, such intraocular lenses comprise some type of optical element and a support, or haptic, coupled thereto for properly positioning and centering the intraocular lens within the eye. Many such lenses are made from polymethylmethacrylate (PMMA), a hard plastic composition. A more recent development in the field of intraocular lenses is the use of a soft, biocompatible material, such as silicone, to manufacture the lenses. Silicone lenses have the advantage of being lighter in situ than PMMA lenses, and because they are flexible, they can be folded to reduce their size during implantation into the eye in accordance with conventional surgical procedures.

A technique which has gained wide acceptance for the removal of the diseased or damaged native lens is called phacoemulsification. The phacoemulsification process is very advantageous because of the extremely small incision required to perform the technique. The incision can be as small as 2–4 millimeters in length. Several prior art attempts have been made to form an intraocular lens injector that would enable the insertion of an intraocular lens through the small phacoemulsification incision without requiring the elongation of the incision.

U.S. Pat. No. 4,681,102 issued on Jul. 21, 1987 to Michael T. Bartell discloses an apparatus and method for the insertion of an intraocular lens through a small incision on the order of several millimeters. The insertion apparatus disclosed by Bartell comprises a load chamber which is utilized to fold a soft intraocular lens into a shape which has a smaller cross-sectional area. The load chamber is comprised of two hinged members which together define a generally cylindrical lumen. Each of the two members includes a flange which extends non-parallel to the cylindrical members at the point of connection and enables manipulation of the cylindrical members from a first open position to a second closed position. The intraocular lens is inserted into the load chamber when the two members are in an open position. The flanges are advanced towards each other causing the two members to form the generally cylindrical chamber. As the two members advance towards each other, the intraocular lens which is inserted in the chamber is compressed in order to conform to the generally cylindrical shape of the members in the closed position.

The loading chamber, as defined above, is placed into an injector portion. The injector portion comprises an insertion cone at one end of the injector portion and a plunger at the other end of the injector portion. The plunger means presses the intraocular lens out of the generally circular lumen of the loading chamber and into the insertion cone. The intraocular lens is further compressed to a smaller diameter by the insertion cone and eventually exits a small tube of an approximately 3 mm diameter at the end of the insertion cone. In use, the Bartell lens injector is positioned such that the tube at the end of the insertion cone is inserted into the small incision made in the eye for the phacoemulsification procedure. Thus, when the lens is pushed out of the insertion cone by the plunger, the lens will be expelled into the interior chamber of the eye.

One disadvantage of the Bartell lens injector is the damage that it often causes to the lens as it is being inserted into the patient's eye. There are two areas of the Bartell injector which have a potential for inflicting damage to the intraocular lens. The first area is the loading chamber. When the lens is inserted in the loading chamber and the two semicircular members are advanced towards each other using the flanges, often the lens does not fold into the cylindrical shape as it was intended. When this occurs, a portion of the lens or the radially extending haptics becomes caught between the flanges and the lens is cut or otherwise damaged. The second area of the Bartell injector which often causes damage is the insertion cone. If the loading chamber is not properly aligned with the insertion cone the lens may be damaged when it is compressed into the insertion cone and may catch on the misaligned components. The main problem with lens damage by a lens injector is that the damage is not always detectable before the lens is inserted into the patient's eye. Once a damaged lens has been inserted into the eye, it is difficult to remove without causing damage to the surrounding eye tissue.

U.S. Pat. No. 4,702,244 entitled "Surgical Device for Implantation of a Deformable Intraocular Lens" issued on Oct. 27, 1987 to Mazzocco discloses another type of surgical device for implantation of an artificial intraocular lens in an eye through a relatively small incision. The device disclosed by Mazzocco includes a chamber for containing the intraocular lens in an unstressed state and for orienting the lens in a prescribed orientation to facilitate lens placement within the eye. The surgical device includes a means for exerting a force on the lens sufficient to deform the lens such that the optical zone is deformed to a substantially smaller cross-sectional diameter than the optical zone in an unstressed state and a means to expel the lens from the device for placement in the eye. The surgical device disclosed by Mazzocco requires the use of an outside force, such as a hydraulic force or a pneumatic force, to force the lens from its unstressed state into a deformed position to enable insertion through the small incision. In the embodiment which compresses the lens from an unstressed state to a stressed state, the lens is propelled toward a small opening at the end of a holding tube. As the lens approaches the opening it is folded back against itself and compressed to fit through the opening. This device is not preferred by doctors because the deformation of the lens is not uniform throughout the lens and is not consistent with every injection. The deformation of the lens varies each time depending on what portion of the lens approaches the opening first.

Another device disclosed in the Mazzocco patent requires the stretching of the lens via two hook members which stretch the lens longitudinally before insertion in the eye. This longitudinal stretching of the lens against the two hook members also may result in damage to the lens at the location where the hook members engage the lens.

Therefore, there exists a need in the prior art for an intraocular lens injector which does not require the use of a hydraulic or pneumatic force to deform the lens. Further, there exists a need for an intraocular lens injector which can compress the lens into a smaller diameter using a mechanical force without causing any damage to the lens.

SUMMARY OF THE INVENTION

The intraocular lens injector of the present invention compresses the diameter of the intraocular lens by rolling the lens into a tight cylindrical tube which can be inserted through a relatively small incision in the eye of approximately 2–4 millimeters in length. In addition, the intraocular lens injector of the present invention is designed to minimize the amount of damage that is inflicted upon intraocular lens during the compression and insertion of the lens.

The intraocular lens injector of the present invention comprises a first compression portion and a second injection portion. The first compression portion comprises a first shuttle member with a scoop end, an intraocular lens receiving channel and a mating cylindrical passageway. The insertion portion of the invention comprises an insertion plunger and an insertion tube which mate with the cylindrical passageway of the compression portion. Preferably, in use, a sterile intraocular lens is placed in the intraocular lens receiving channel in an uncompressed state. The intraocular lens shuttle is inserted into the intraocular lens receiving channel, and the scoop end urges the intraocular lens towards the cylindrical passageway. The scoop end of the intraocular lens shuttle mates with the opening of the cylindrical passageway to form a complete cylinder when the shuttle member is extended into its furthest position. As the shuttle advances the lens towards the cylindrical passageway, a first end the intraocular lens enters the cylindrical passageway and continues to advance until it contacts a far wall of the cylindrical chamber. Once the first end of the lens contacts the far wall, the lens begins to move up the wall until the first end of the intraocular lens engages with a second flat portion of the intraocular lens which has just been introduced into the cylindrical passageway. As the intraocular lens shuttle continues to advance the intraocular lens into the chamber, the first end of the lens will further engage with the flat portion of the lens and will begin to roll upon itself into a tightly rolled spiral. The shuttle is continuously advanced, forcing the remaining portions of the intraocular lens to roll about the intraocular lens already in the cylindrical passageway until the shuttle is completely advanced and the intraocular lens is compressed into a tightly rolled spiral which is the diameter of the compression portion. Into the open end of the cylindrical passageway is advanced an insertion plunger which advances the intraocular lens from the compression portion of the lens injector into the injection portion of the lens injector.

In one embodiment of the invention, the insertion plunger is continually advanced through the cylindrical passageway into the insertion tube which is placed within an incision in the ocular tissue of the eye. The advancement of the intraocular lens by the insertion plunger will force the lens out of the insertion tube and into the eye. In another embodiment, the lens is advanced by the insertion plunger into the insertion tube of the intraocular lens injector, which is then detached from the compression portion of the intraocular lens injector. The insertion tube is attached to an insertion tube. Preferably, the insertion handle comprises an insertion sleeve and an insertion rod. The insertion tube is connected to one end of the insertion sleeve and the insertion rod is connected to the other end. The insertion handle is inserted through the small incision in the optical tissue of the eye, and the insertion rod of the insertion handle is continually advanced until the lens is expelled from the insertion tube into the eye.

BRIEF DESCRIPTION OF THE DRAWINGS

FIG. 6a is a sectional view of the lens injector of the present invention taken along the line 6a of FIG. 6b with an intraocular lens inserted therein.

FIG. 6b is a sectional view taken along the line 6b of the lens injector as illustrated in FIG. 6a.

FIG. 7a is a sectional view of the lens injector of the present invention illustrating the intraocular lens beginning to compress into the rolled configuration.

FIG. 7b is a sectional view of the lens injector with the intraocular lens in the same position as illustrated in FIG. 7a.

FIG. 8a is a sectional view of the lens injector with the intraocular lens in the completed rolled configuration.

FIG. 8b is a sectional view of the intraocular lens injector with the intraocular lens in the same position as illustrated in FIG. 8a.

DETAILED DESCRIPTION OF THE PREFERRED EMBODIMENT

Figure 1:
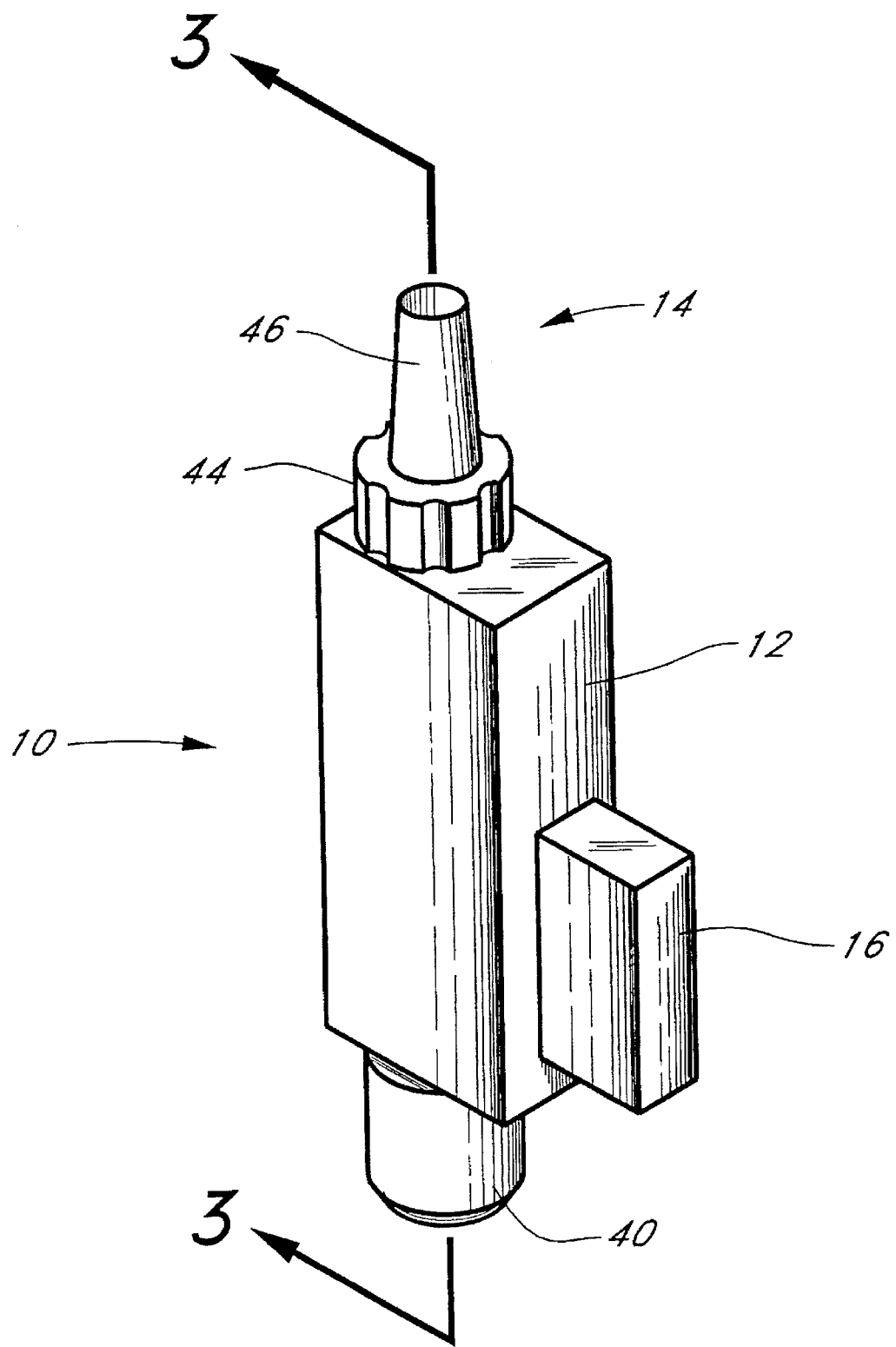
FIG. 1 is a perspective view of a preferred embodiment of the lens injector of the present invention.
Figure 2:
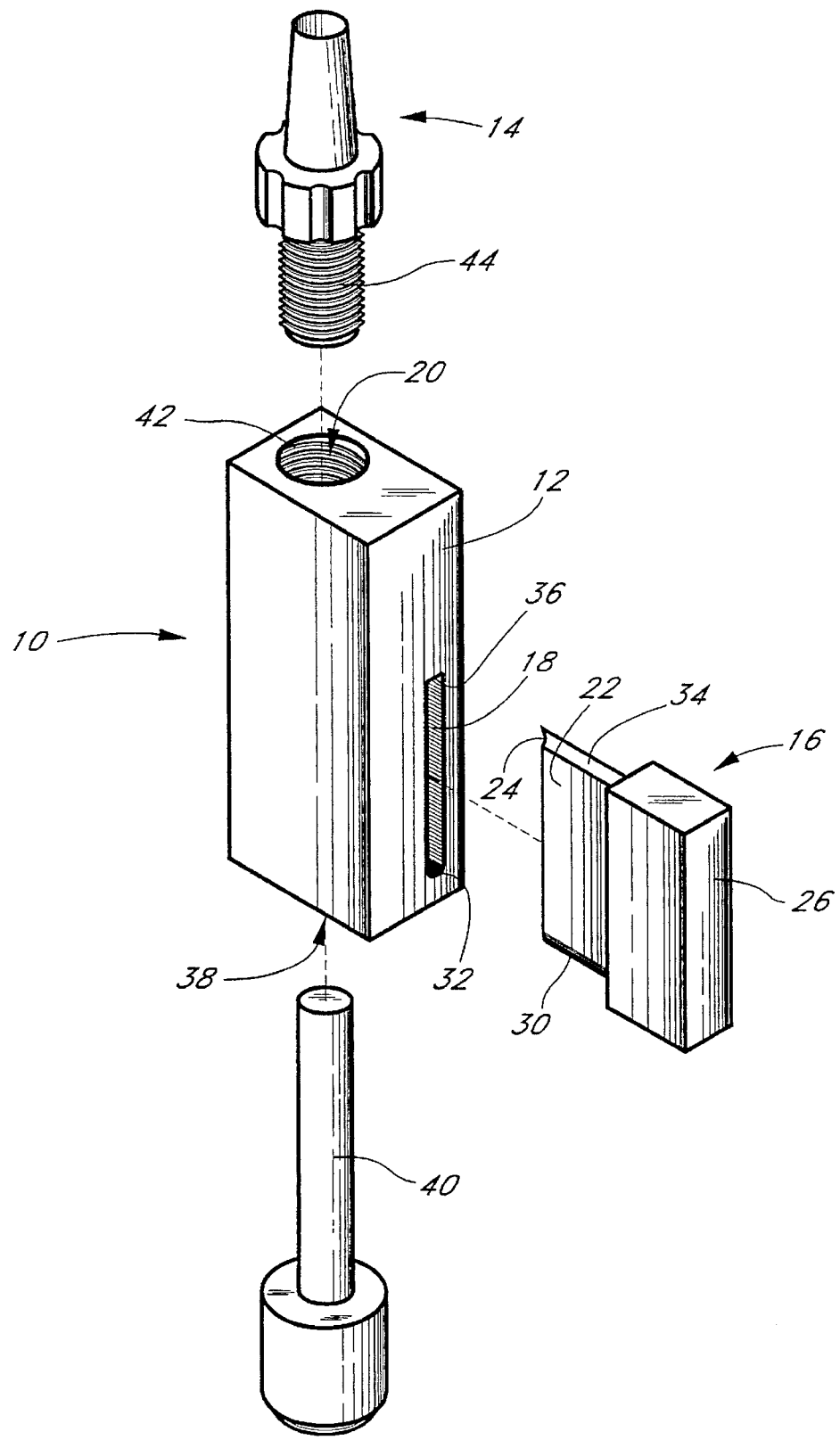
FIG. 2 is an exploded perspective view of the lens injector as illustrated in FIG. 1.
Figure 3:
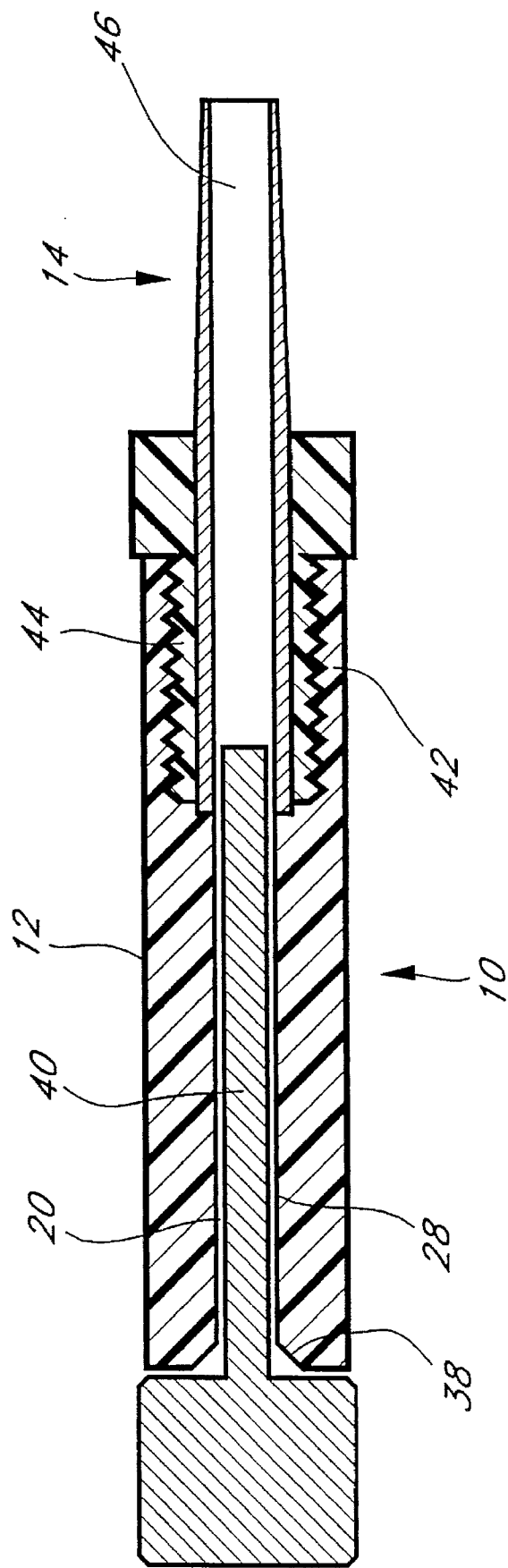
FIG. 3 is an cross-sectional view of the lens injector through the line 3—3 illustrated in FIG. 1.
Figure 4:
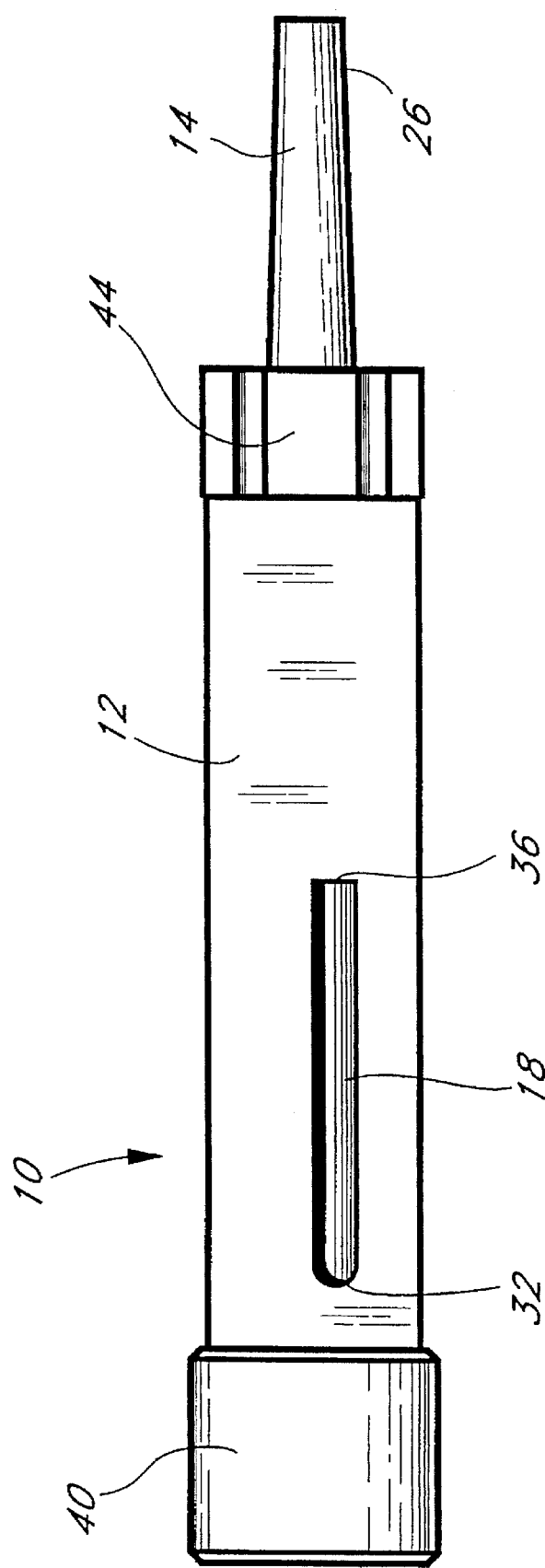
FIG. 4 is a right side view of the lens injector illustrated in FIG. 1.

The present invention provides an improved intraocular lens injecting device for use in inserting an intraocular lens through a small incision in the ocular tissue, such as those which are employed with the phacoemulsification technique of cataract removal.

FIGS. 1–4 illustrate a preferred embodiment of the lens injector of the present invention which compresses and injects an intraocular lens into an eye of a patient. The preferred embodiment of the intraocular lens injector 10 of the present invention comprises a compression portion 12 and a insertion portion 14. The compression portion comprises a shuttle member 16, an intraocular lens receiving channel 18 and a mating cylindrical passageway 20.

The shuttle member 16 comprises a thin, rectangular-shaped pushing member 22 with a concave scoop end 24 and a rectangular handle portion 26 which is thicker than the pushing member 22 to enable a user to easily manipulate the shuttle member 16. The shuttle member 16 is designed such that the pushing member 22 fits tightly within the intraocular lens receiving channel 18 and the concave scoop end 24 terminates tangential to a bottom surface 28 of the cylindrical passageway 20. Preferably, the scoop end 24 of the shuttle member 16 mates with the cylindrical passageway 20 to form a complete cylinder when the intraocular lens shuttle member 16 is completely inserted into the intraocular lens receiving channel 18.

The shuttle member 16 is preferably keyed to match a compatible keying means on the intraocular lens receiving channel 18 such that the shuttle member 16 can only be inserted into the lens receiving channel in only one direction. In one embodiment, the keying means is formed by rounding a first end 30 of the pushing member 22 and rounding a corresponding first end 32 of the intraocular lens receiving channel 18 while squaring an opposite second end 34 of the pushing member 22 and squaring the corresponding opposite second end 36 of the intraocular lens receiving channel 18 such that the shuttle member 16 can only be inserted when the scoop end 24 is inserted tangential to the bottom surface 28 of the cylindrical passageway 20.

The cylindrical passageway 20 extends longitudinally through the compression portion 12 of the intraocular lens injector 10. A first end 38 of the cylindrical passageway 20 is open and enables the insertion of an insertion plunger 40 which urges the intraocular lens from the compression portion 12 into the insertion portion 14 of the intraocular lens injector 10. The cylindrical passageway 20, or rolling chamber, defines the compressed diameter of the intraocular lens when it is rolled upon itself into a spiral defined by the dimensions of the compression portion 12. Preferably, the inner diameter of the cylindrical passageway 20 is approximately 2–3 mm. More preferably, the inner diameter of the cylindrical passageway 20 is as small as 1 mm for intraocular lenses of a reduced thickness. The intraocular lens receiving channel 18 preferably intersects the cylindrical passageway at a right angle and is off-axis to the passageway 20 at the intersection. A second end 42 of the cylindrical passageway 20 terminates at the insertion portion 14. Preferably, the second end 42 of the compression portion 12 is threaded to enable the attachment and removal of the insertion portion 14 from the compression portion 12.

The insertion portion 14 comprises a threaded attachment member 44 concentric with an insertion tube 46. Preferably, the threaded attachment member 44 utilizes a thread size which is identical to the threaded second end 42 of the insertion portion 12. It is important that the compression portion 12 and the insertion portion 14 be perfectly mated, such that there is no uneven ridge at the joining seam which may catch the intraocular lens and potentially damage the lens. The insertion tube 46 is preferably of a 1–3 millimeter inner diameter, which is uniform throughout the length of the insertion tube 46. The cylindrical passageway 20 and the insertion tube are concentric and form an injection channel of uniform diameter through which the intraocular lens is inserted into the eye of the patient. The outer diameter of the insertion tube 46 may be slightly tapered at the end to enable the insertion tube 46 to be placed into a small incision in the ocular tissue while being structurally sound. Preferably, the outer diameter of the insertion tube 46 is approximately 1–4 mm. The wall thickness of the insertion tube 46 is between approximately 0.1 to 0.3 mm depending on the material from which the insertion tube 46 is made. The type of mating threads on the attachment portion 44 and the second end 42 of the insertion portion 12 can be of the conventional screw-type fitting, a luer-lock fitting, bayonet, or any type of attachment known to those of skill in the art.

Preferably, the compression portion 12 is formed of a composite material, such as Teflon, polypropylene, polyethylene, polysulfone, polymethylpentene, polyvinyladine fluoride, or any other polymeric composite material known to one of skill in the art. The shuttle member 16 is preferably made from the same material as the compression portion 12. Alternatively, the cylindrical passageway 20 is formed from hypodermic metallic tubing. Further, the attachment member 44 is preferably made of the same type of composite material as the compression portion 12 to enable a smooth mating of similar materials. Further, the passageway 20, the scoop end 24 of the shuttle member 16 and the insertion tube 46 are line-bored after they are assembled to ensure a perfectly mated contiguous passageway 20 through the compression 12 and insertion portions 14 of the injector 10. In one embodiment, all of the parts of the compression portion 12 are injection molded in one mold to ensure that all of the elements which make up the passageway 20 are perfectly mated with each other to form a contiguous passageway. Preferably, the insertion tube 46 and the insertion plunger 40 are made from aluminum, stainless steel, titanium or any other material known to one of skill in the art, which can be easily machined to their desired shape and does not easily rust or corrode. In addition, if any element which comes into contact with the intraocular lens is made from a metallic material, the element must be chemically passivated or pickled to remove any impurities which could transfer to the lens. If such impurities are transferred to the lens, toxic substances other known adverse syndromes may be introduced into the patient's eye upon implantation. Further, it is important that all of the pieces which interact with the intraocular lens are de-burred, blended smooth, and polished to a high luster to prevent any damage to occur when the lens comes into contact with an element of the intraocular injector device 10. The end of the insertion plunger 40 is preferably rounded and polished so that there are no sharp edges which come into contact with the intraocular lens.

Figure 5:
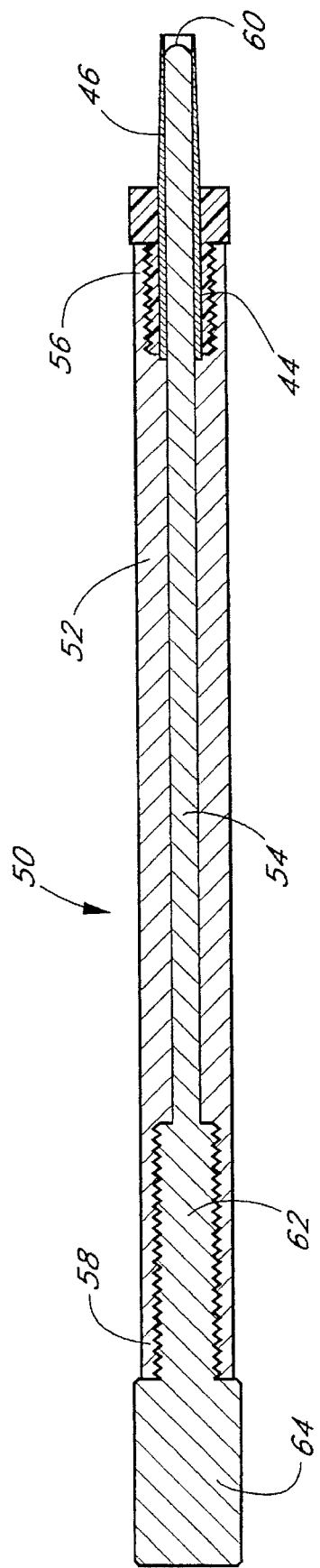
FIG. 5 is a cross-sectional view of an injection handle which is used with one embodiment of the lens injector of the present invention.

FIG. 5 illustrates an injection handle 50 which can be used with the embodiment of the lens injector 10 illustrated in FIGS. 1–4. The injection handle 50 illustrated in FIG. 5 comprises an injection sleeve 52 and an injection rod 54. The injection sleeve 52 is threaded at a first end 56 to mate with threads of the attachment device 44 of the insertion portion 14. A second opposite end 58 of the injection sleeve 52 is preferably threaded to mate with the threads on the injection rod 54.

When used with the lens injector of FIGS. 1–4, the insertion portion 14 is detached from the compression portion 12 of the injector 10 illustrated in FIGS. 1–4 and is connected to the first end 56 of the injection sleeve 52. The threads on the first end 56 of the injection sleeve 52 are sized to match the threads on the attachment device 44 of the insertion portion 14 to enable a smooth connection between the two mating pieces.

A first end 60 of the injection rod 54 is preferably machined to a rounded finish similar to that of the insertion plunger 40 of the lens injector 10. A second opposite end 62 of the injection rod 54 is preferably threaded to enable a slow guided insertion of the intraocular lens and preferably terminates with an elongated handle 64 to enable the user to accurately control the progression of the injection rod 54.

Preferably, the injection sleeve 52 is a narrow cylindrical design which is long enough to enable the user to easily manipulate the injection handle 50 to direct the handle to the desired insertion location. Further, the injection handle 50 should have a small radius such that the handle 50 does not interfere with the patient's anatomy, i.e., the patient's nose or eye socket, during the insertion of the intraocular lens.

Preferably, the injection handle 50 is made from aluminum, stainless steel, titanium or any other material known to one of skill in the art which is easy to machine and does not easily rust or corrode when sterilized prior to the surgery. In addition, the injection rod 54 is preferably made from a similar material as the remainder of the injection handle. Further, it is important that all of the elements which interact with the intraocular lens are de-burred, blended smooth, chemically cleaned and polished to a high luster to prevent any damage to occur when the lens comes into contact with any element.

The intraocular lens injector 10 can be used to both compress and insert an intraocular lens 65 into the patient's eye. Preferably, the intraocular lens comprises an optical element located in a central portion 72 of said lens 65 and a pair of haptics 66 extending from said optical element which are formed as a one-piece unit. However, the present invention can be used with any of a variety of multiple piece intraocular lenses which comprise an optical element and two haptic which are made from a different type of material than the lens element. The optical element is thicker than the haptics 66 and is curved in accordance with the vision correction which is required by the patient. Advantageously, if an intraocular lens 65 with a thinner optical element is used, the intraocular lens injector 20 of the present invention can compress the intraocular lens 65 to a smaller diameter. Referring to FIGS. 6a and 6b, the intraocular lens 65 is first placed within the intraocular lens receiving channel 18 in the compression portion 12 of the injector 10. As illustrated in FIG. 6b, the lens 65 is preferably positioned such that the haptics 66 are perpendicular to the side walls 67 of the intraocular lens receiving chamber 18. The shuttle member 16 is then inserted into the intraocular lens receiving chamber 18 with the scoop end 24 such that the scoop end 24 is tangential to the bottom surface 28 of the cylindrical passageway 20. Preferably, the entire compression portion 12, including the cylindrical passageway 20 and the intraocular lens receiving chamber 18, is lubricated with a sterile visco-elastic material, such as Helon, which is manufactured by Khabi-Pharmacia. The visco-elastic material lubricates all of the internal passageways, such as the lens receiving channel 18, the cylindrical passageway 20, and the insertion tube 46, to decrease the level of friction in these passageways. Friction between the lens 65 and the surface of the injector may cause damage to the lens 65; therefore, the use of a visco-elastic material is desirable.

As illustrated in FIGS. 7a and 7b, the shuttle 16 is gently manually urged forward and pushes the intraocular lens 65 towards the cylindrical passageway 20. The intraocular lens 65 advances into the cylindrical passageway 20 and a first end 70 of the intraocular lens 65 abuts a far wall 68 of the cylindrical passageway 20 which is across from the entry point of the intraocular lens receiving channel 18 into the cylindrical passageway 20. Once the intraocular lens 65 comes into contact with the far wall 68, continued urging of the intraocular lens 65 into the cylindrical passageway 20 causes the lens 65 to climb the far wall 68 and proceed in a circular path around the cylindrical passageway 20. The tangential entry of the lens 65 to the bottom surface 28 of the cylindrical passageway 20 forces the lens 65 to follow the walls of the cylindrical passageway 20 and to take on a cylindrical shape.

As illustrated in FIGS. 8a and 8b, the lens 65 will continue to progress around the cylindrical passageway 20 until the first end 70 of the lens 65 comes into contact with the central portion 72 of the intraocular lens 65 which has just advanced into the cylindrical passageway 20. The first end 70 of the lens 65 will come into contact with the central portion 72 of the lens 65 rather than the bottom surface 28 of the passageway 20, since the lens 65 is wider than the circumference of the passageway 20.

Once the first end 70 of the lens 65 comes into contact with the central portion 72 of the lens 65 which is advancing into the chamber, the first end 70 of the lens 65 will roll up against the central portion 72 of the lens 70 and begin to form a tight spiral within the confines of the cylindrical passageway 20. As the intraocular lens 65 is continually urged into the cylindrical passageway 20, the intraocular lens 65 will continue to roll up about itself and form a tight spiral. As the intraocular lens 65 is continually compressed into the tight spiral shape, the axial length of the rolled up lens 65 will increase to enable the lens 65 to continue to compress to fit within the confines of the cylindrical passageway 20.

As the intraocular lens 65 is compressed in the cylindrical passageway 20, the length of the compressed intraocular lens 65 increases to enable the further compression of the lens 65 into the cylindrical shape of reduced diameter. When the shuttle 16 has been advanced the entire length of the intraocular lens receiving channel 18 and the scoop end 24 mates with the opening into the cylindrical passageway 20 to form a complete cylinder, the lens 65 is compressed into the smallest diameter possible. As illustrated in FIG. 8b, once the lens 65 is compressed into a spiral of the final reduced diameter, the axial length of the lens 65 has increased to enable the lens to compress into the confines of the cylindrical passageway 20. Preferably, the elongated length of the compress intraocular lens 65 is less than the length of the shuttle member 16. This ensures that the shuttle member 16 does not damage the lens 65 by clipping the elongated lens 65 with either of the ends 30, 34 of the shuttle member 16.

Figure 9:
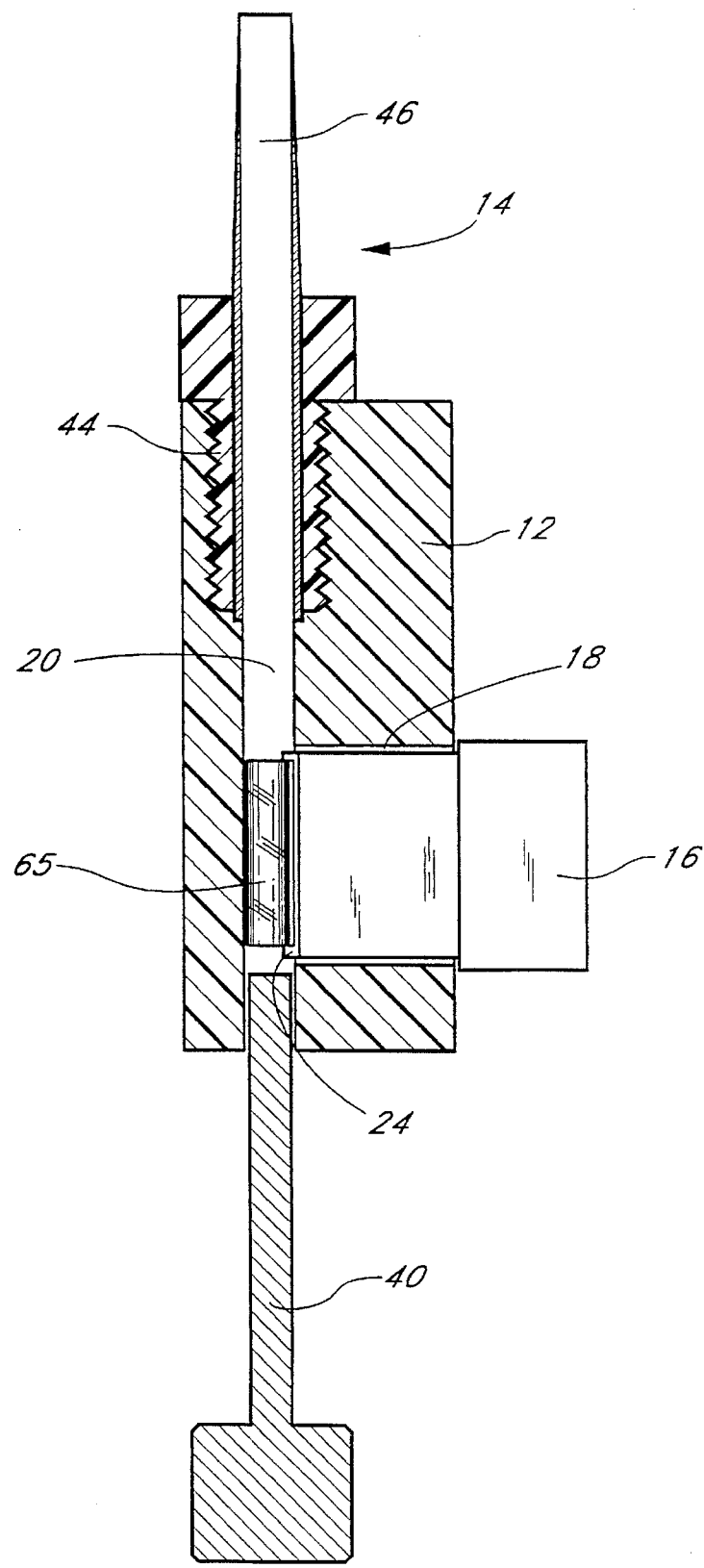
FIG. 9 is a sectional view of the intraocular lens injector with the insertion rod introduced into the cylindrical passageway.
Figure 10:
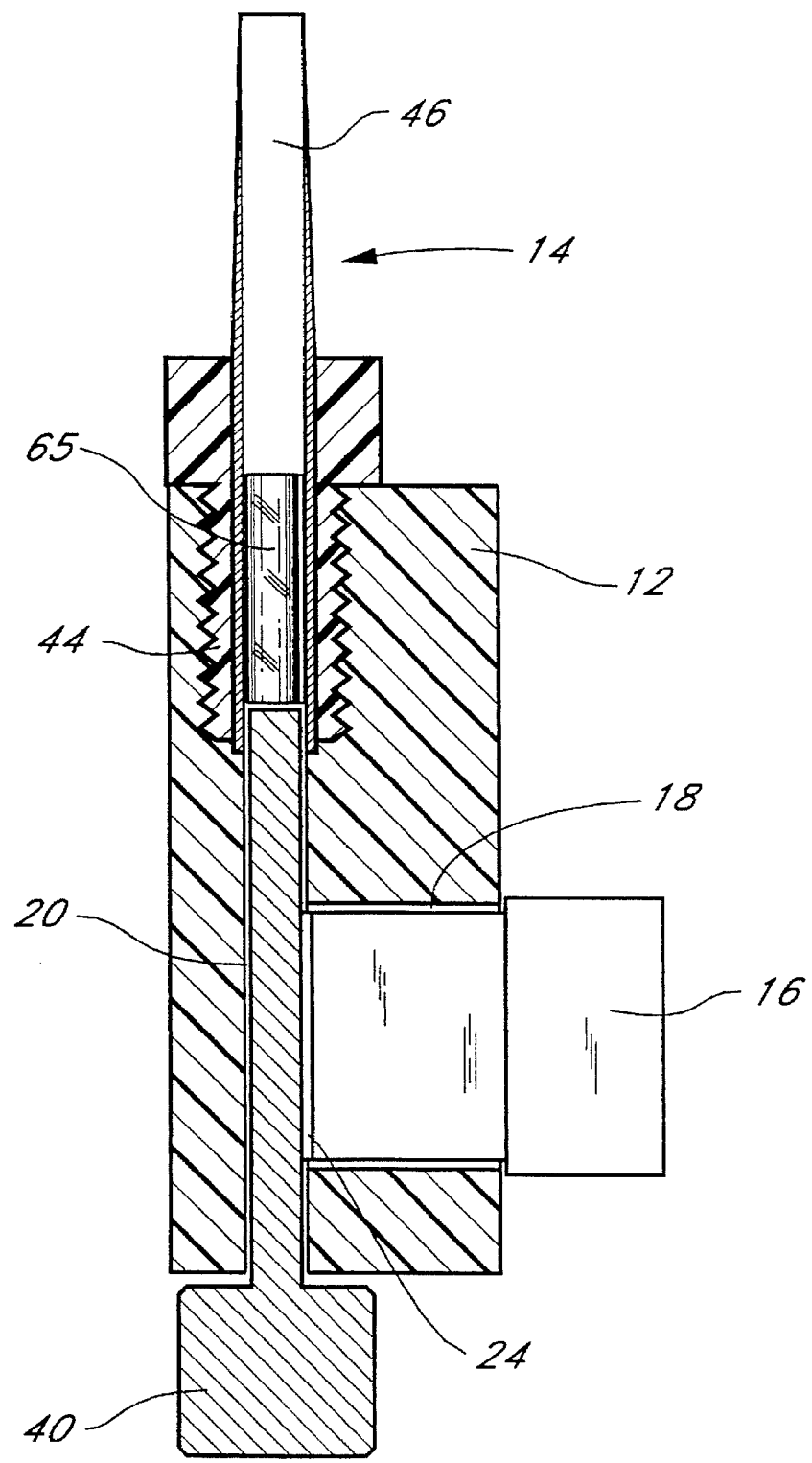
FIG. 10 is a sectional view of the intraocular lens injector with the insertion rod advanced to its fully inserted position and the intraocular lens positioned in the insertion tube.

As illustrated in FIGS. 9–10, an insertion plunger 40 is introduced into the second end 42 of the cylindrical passageway 20 and is advanced until it comes into contact with the intraocular lens 65. The insertion plunger 40 is continuously advanced and, in turn, pushes the intraocular lens 65 through the cylindrical passageway 20 and into the mating insertion tube 46. As illustrated in FIG. 10, the insertion plunger 40 progresses through the cylindrical passageway 20 until the compressed intraocular lens 65 is completely contained within the insertion tube 46.

In an alternate embodiment of the present invention, the insertion plunger 40 is elongated such that the insertion tube 46 can be placed directly into an eye of the patient and the lens 65 is injected directly from the insertion tube 46 into the patient's eye.

In a preferred embodiment, the insertion portion 14, with the lens 65 rolled up inside, is detached from the compression portion 12 of the lens injector 10 and is attached to the injection handle 50, as illustrated in FIG. 5. Preferably, the insertion tube 46 is attached onto the first end 56 if the injection sleeve 52 via the attachment device 44 to form a lightweight and streamlined lens injector to insert the sterile lens 65 into the eye of a patient. The injection rod 54 is introduced into the second end 58 of the injection sleeve 52 and is advanced through the injection sleeve 52 and into the injection tube 46. As the injection rod 54 approaches the insertion tube 54, the threads on the injection rod 54 will engage with the threads on the second end 58 of the injection sleeve 52. Turning of the injection rod 54 within the threads of the injection sleeve 52 will slowly advance the injection rod 54 until it comes into contact with the intraocular lens 65 in the insertion tube 46.

Figure 11:
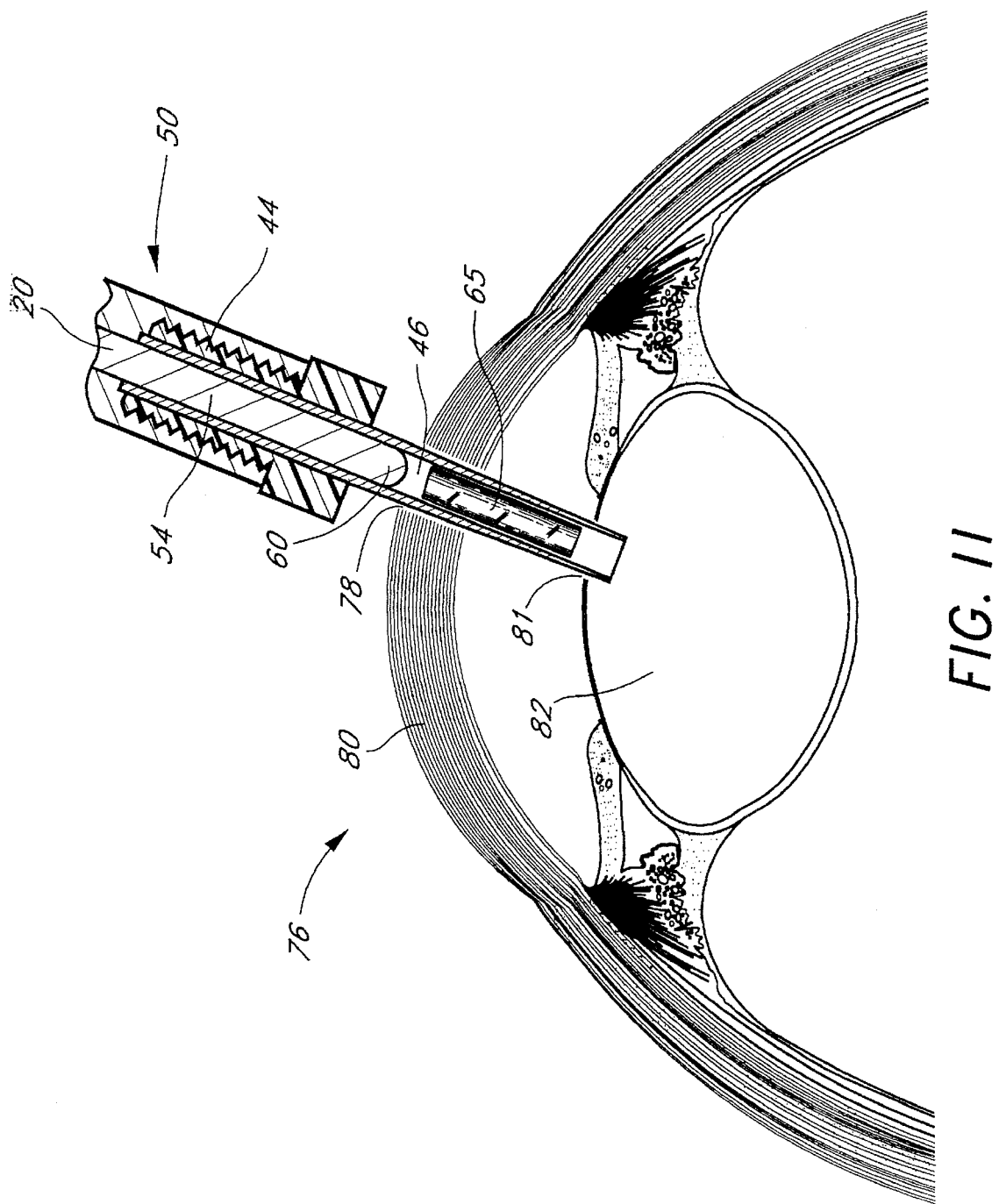
FIG. 11 is a sectional view of the injection handle as illustrated in FIG. 5 in combination with the injection tube containing an intraocular lens in the compressed state, wherein the intraocular lens is inserted through a small incision into the lens capsule of an eye.

As illustrated in FIG. 11, at this point, the injection handle 50 is positioned such that the insertion tube is introduced into an eye 76 through a small 2–4 millimeter incision 78 in a cornea 80 of the eye 76 formed by the phacoemulsification process which previously removed the native lens of the eye. Next, the insertion tube 46 is preferably inserted through a small incision 81 in the lens capsule 82. The insertion tube 46 is positioned such that the compressed lens 65 exits the insertion tube 46 in the desired position. The injection rod 54 is continually advanced as the second end 62 of the injection rod 54 is turned within the threads of the second end 58 of the injection sleeve 52 which advances the intraocular lens 65 until it is forced out of the injection tube 46 and into the lens capsule 82. As the lens 65 is expelled from the injection tube 46, the lens 8 will expand from its compressed state into its original unstressed state and the user will position the injection handle 50 in such a manner that the lens 65 is expelled into the desired location and orientation within the lens capsule 82.

Figure 12:
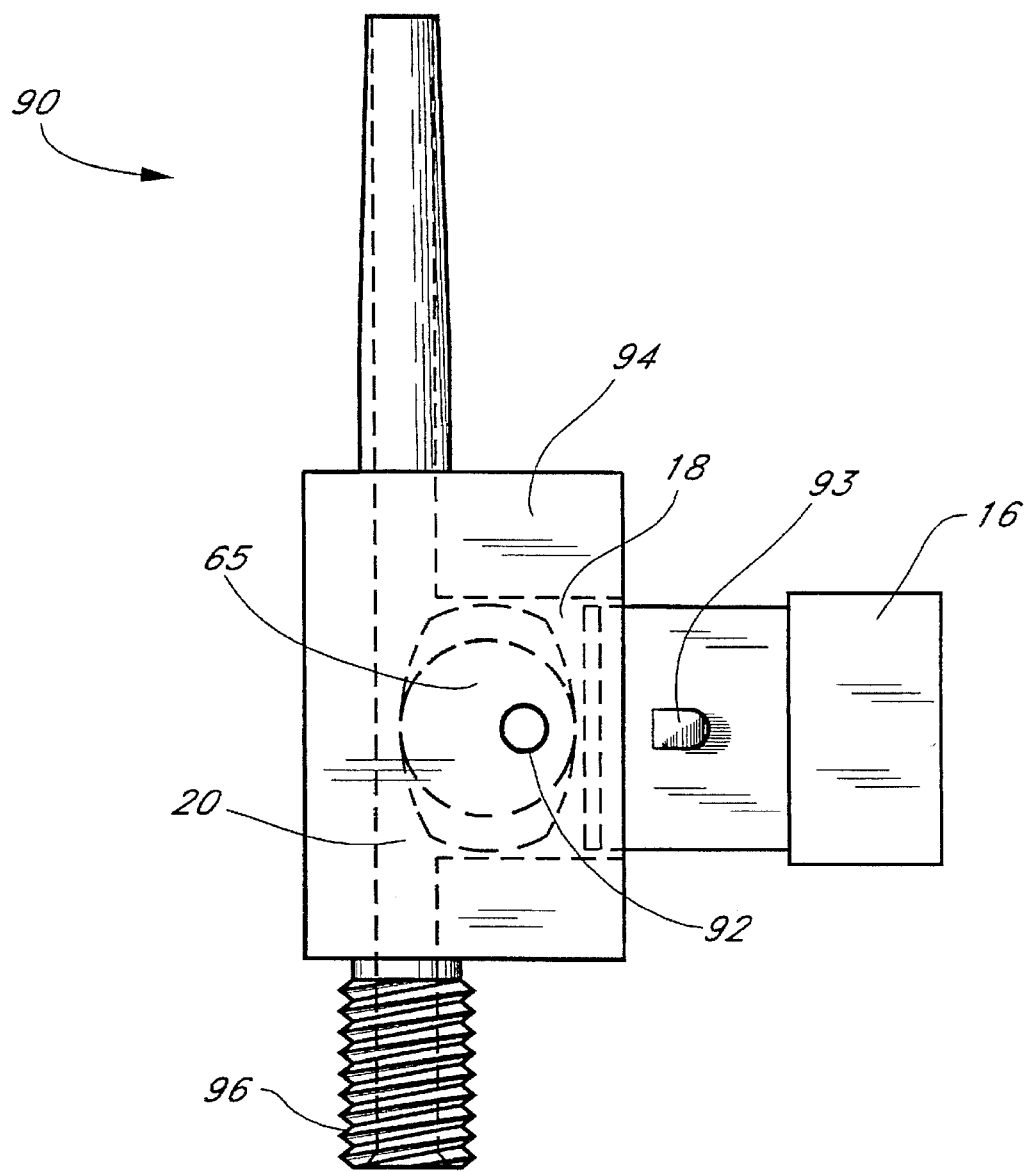
FIG. 12 is a top view of a second embodiment of the intraocular lens injector of the present invention.
Figure 13:
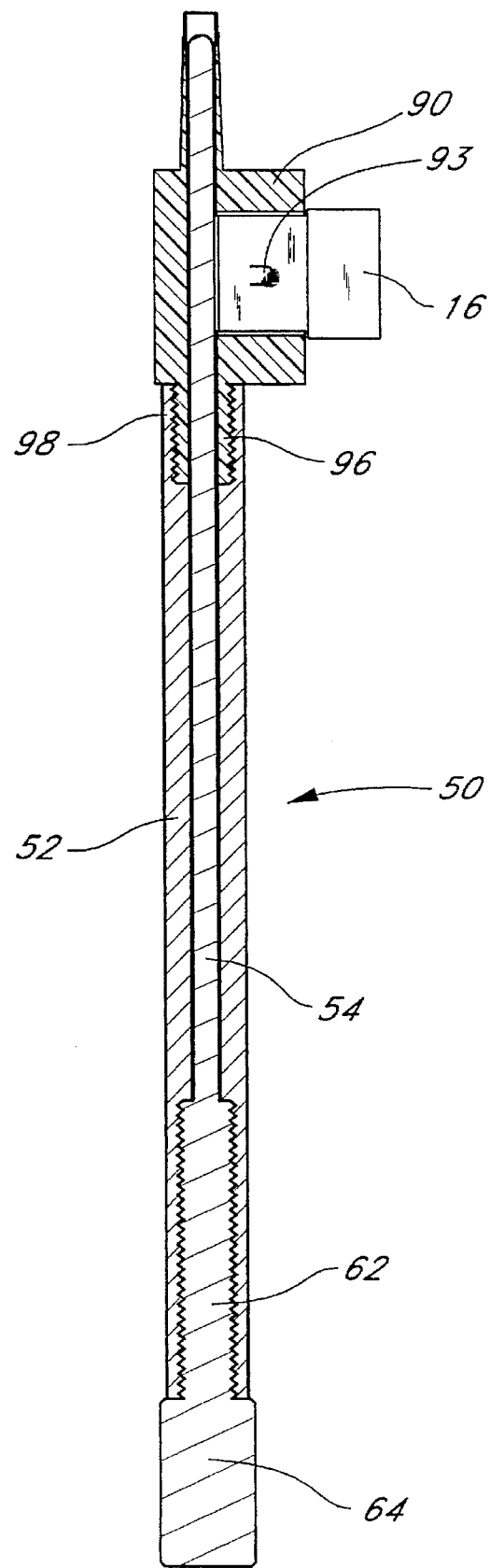
FIG. 13 is a sectional view of the second embodiment of the intraocular lens injector of the present invention in combination with the injection handle as illustrated in FIG. 5.

FIGS. 12–13 illustrate an alternative embodiment of the intraocular lens injector in which the compression portion 12 and insertion portion 14 are formed from a single piece 90 of composite material which can be disposed of after each use. Preferably, a viewing hole 92 is formed in a top surface 94 of the one-piece compression and insertion portion 90 to enable the user to view the intraocular lens 65 within the receiving channel 18 to verify that it has been properly aligned within the channel 18. In one embodiment, a small raised button detent 93 is molded onto the shuttle member 16 which will index and audibly snap into place within the viewing hole 92 when the shuttle has been completely inserted within the intraocular lens receiving channel and the scoop end 24 of the shuttle is in proper alignment with the opening to the cylindrical passageway 20. Further, the raised button 93 will act to resist the compression forces on the lens 65 and will hold the shuttle member 16 in alignment with the cylindrical passageway 20 to prevent any damage from occurring to the lens during injection. As illustrated in FIG. 13, the single piece compression and injection portion 90 is mated to a tubular injection handle 50 using threads 96 and a set of mating threads 98. The mating threads 96 and 98 may be of a standard screw type thread, a luer-lock thread or any other connection means known to one of skill in the art. The first end 56 of the injection sleeve 52 is mated with an injection rod 54. Preferably, the second end 58 of the injection sleeve 52 is threaded to enable the injection rod 54 to be slowly advanced into the one-piece compression and injection unit 90. Preferably, the advancement of the injection rod 54 is controlled by turning the injection rod 54 within the threaded second end 58 of the injection handle 50. Preferably, the injection handle 50 and insertion rod 54 are formed of a stainless steel, titanium, or aluminum material which can be easily machined into the desired configuration. In addition, the one-piece compression and insertion portion 90 is made from a composite or plastic material which is inexpensive, as the embodiment of the one-piece compression and injection portion 90 is preferably disposable.

In use, the injection rod 54 is placed within the tubular steel handle 50 such that the rod 54 is positioned just above the opening of the IOL receiving channel 18 and the threads of the insertion rod 54 begin to engage the threads of the second end 58 of the injection sleeve 52. The intraocular lens 65 is then placed within the receiving channel 18 and the alignment of the intraocular lens 65 is checked through the viewing hole 92. As described above, the shuttle member 16 is advanced toward the cylindrical passageway 20 which advances the lens 65 into the cylindrical passageway 20 and the lens 65 begins rolling upon itself. Once the lens 65 is completely advanced into the cylindrical passageway 20, the raised button 93 on the shuttle member 16 snaps into place within the viewing hole 92, to maintain the alignment of the shuttle member 16 with the cylindrical passageway 20 and to prevent the compression force of the lens from forcing the shuttle 16 out of alignment. At this point, the lens 65 is formed into the elongated tight spiral configuration which conforms to the diameter of the cylindrical passageway 20. The injection rod 54 is advanced by turning the rod 54 in the threads on the second end 58 of the injection sleeve 52 to slowly advance the insertion rod 54 and the compressed intraocular lens 65. The intraocular lens 65 is slowly advanced through the cylindrical passageway 20 and out the opening 100 at the end of the once piece compression and injection portion 90.

In one embodiment, the one-piece unit 90 is made from a disposable plastic material which can be thrown away after each use. This disposable one-piece compression and injector unit 90 is advantageous, as it does not require the continual sterilization of the injection piece 90 for each patient. Further, the user does not have to be concerned with the problems associated with wear and tear on the injector which may result in rough edges or barbs forming within the lens injector which may damage the intraocular lens 65 upon compression or insertion of the lens.

The lens can be stored within the lens receiving channel 18 in the one-piece compression injection portion 90 during shipping, so that the only assembly required is attaching the one-piece compression and injection portion 90 to the injection handle 50. Preferably, the shuttle member 16 is held in a storage position by a detent or strap (not shown) which extends from the shuttle member 16. The storage position is such that the lens 65 remains within the lens receiving channel 18 without being compressed by the shuttle member 16. Preferably, the one-piece compression and injection portion 90 is sterilized and sealed in the storage position before the one-piece unit 90 is shipped.

Once the lens 65 is to be inserted, the seal is broken and the one-piece unit 90 is attached to the injection handle 50. The storage detent on the shuttle member 16 is broken by applying a force to the shuttle member 16 which sheers the storage detent and enables advancement of the shuttle member 16. The shuttle member 16 is advanced and the lens 65 is compressed into the cylindrical shape of the cylindrical passageway 20. The alignment and progression of the lens 65 within the intraocular lens receiving channel 18 can be verified through the viewing hole 92 until the lens 65 is completely inserted into the cylindrical passageway 20. This one-piece embodiment 90 is advantageous over prior art lens injectors as the one-piece compression and insertion portion 90 can be used as both a shipping container and as a means for compressing and inserting the lens 65 into the eye.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. A method of inserting an intraocular lens into a small incision comprising the steps of:

providing an intraocular lens in an unstressed state;

rolling said lens upon itself into a tightly rolled spiral within a passageway, said passageway having an opening; said rolling step comprising:

urging said unstressed intraocular lens into said passageway through said opening;

contacting a far wall of said passageway opposite said opening with a first edge of the intraocular lens;

continually urging said intraocular lens into said passageway, as said first edge of said lens moves along said wall of the passageway until said first edge of the intraocular lens engages a second portion of the intraocular lens which has just been introduced into the passageway; continually urging said intraocular lens into said passageway, as said lens rolls upon itself into a tightly rolled spiral;

continually urging said intraocular lens into said passageway, until the entire intraocular lens has rolled upon itself and the intraocular lens is compressed to a diameter of the passageway; and urging said tightly rolled lens into the eye of the patient.

2. A method of inserting an intraocular lens into a small incision as defined in claim 1, wherein said passageway has a diameter of 1–3 mm.

3. A method of rolling an intraocular lens upon itself, comprising the steps of:

urging an intraocular lens in an unstressed state into a passageway through a lens receiving opening in the side of said passageway; and simultaneously urging said lens against said passageway opposite said opening causing an advancing edge of said lens to slide against said passageway and to roll upon the remainder of the lens within said passageway.

* * * * *